(12) United States Patent
Accardi et al.

(10) Patent No.: US 9,324,825 B2
(45) Date of Patent: Apr. 26, 2016

(54) MANUFACTURING METHOD OF A GRAPHENE-BASED ELECTROCHEMICAL SENSOR, AND ELECTROCHEMICAL SENSOR

(71) Applicant: STMicroelectronics S.r.l., Agrate Brianza (IT)

(72) Inventors: Corrado Accardi, Ragusa (IT); Stella Loverso, Catania (IT); Sebastiano Ravesi, Catania (IT); Noemi Graziana Sparta, Catania (IT)

(73) Assignee: STMICROELECTRONICS S.R.L., Agrate Brianza (IT)

( * ) Notice: Subject to any disclaimer, the term of this patent is extended or adjusted under 35 U.S.C. 154(b) by 0 days.

(21) Appl. No.: 13/917,379

(22) Filed: Jun. 13, 2013

(65) Prior Publication Data
US 2013/0334579 A1    Dec. 19, 2013

(30) Foreign Application Priority Data

Jun. 14, 2012  (IT) .............................. TO2012A0516

(51) Int. Cl.
| | |
|---|---|
| *G01N 27/403* | (2006.01) |
| *H01L 29/66* | (2006.01) |
| *G01N 27/414* | (2006.01) |
| *B01L 3/00* | (2006.01) |

(52) U.S. Cl.
CPC ........ *H01L 29/66053* (2013.01); *G01N 27/414* (2013.01); *H01L 29/66* (2013.01); *B01L 3/502707* (2013.01)

(58) Field of Classification Search
CPC .............................................. H01L 31/022425
See application file for complete search history.

(56) References Cited

U.S. PATENT DOCUMENTS

| | | | |
|---|---|---|---|
| 7,598,546 B1* | 10/2009 | Chou ................ | G01N 27/4145 257/253 |
| 2008/0023327 A1* | 1/2008 | Douglas ................... | 204/403.14 |
| 2010/0320437 A1* | 12/2010 | Gordon et al. .................... | 257/9 |
| 2012/0161257 A1* | 6/2012 | Friza et al. ..................... | 257/416 |
| 2014/0145735 A1* | 5/2014 | Koester ............... | G01N 27/227 324/686 |

OTHER PUBLICATIONS

Giacchetti B. M. et al., "CVD-Grown Graphene Solution-gated Field Effect Transistors for pH Sensing," Mater. Res. Soc. Symp. Proc. vol. 1283, 6 pgs., 2011.

(Continued)

*Primary Examiner* — Zandra Smith
*Assistant Examiner* — Andre' C Stevenson
(74) *Attorney, Agent, or Firm* — Seed IP Law Group PLLC

(57) ABSTRACT

A manufacturing method of an electrochemical sensor comprises forming a graphene layer on a donor substrate, laminating a film of dry photoresist on the graphene layer, removing the donor substrate to obtain an intermediate structure comprising the film of dry photoresist and the graphene layer, and laminating the intermediate structure onto a final substrate with the graphene layer in electrical contact with first and second electrodes positioned on the final substrate. The film of dry photoresist is then patterned to form a microfluidic structure on the graphene layer and an additional dry photoresist layer is laminated over the structure. In one type of sensor manufactured by this process, the graphene layer acts as a channel region of a field-effect transistor, whose conductive properties vary according to characteristics of an analyte introduced into the microfluidic structure.

31 Claims, 8 Drawing Sheets

(56) References Cited

OTHER PUBLICATIONS

He, R. X. et al., "Solution-gated graphene field effect transistors integrated in microfluidic systems and used for flow velocity detection," Nano Letters (12):1404-1409, 2012.

Ohno, Y. et al., "Electrolyte-Gated Graphene Field-Effect Transistors for Detecting pH and Protein Adsorption," Nano Letters 9(9):3318-3322, 2009.

Pandey, D. K. et al., "Graphene Based Sensor Development," Apr. 28, 2009.

Vulto, P. et al., "Microfluidic channel fabrication in dry film resist for production and prototyping of hybrid chips," Lab Chip, vol. 5, pp. 158-162, 2005.

Bersini, "Progettazione di un sistema microfluidico per test farmacologici," Tesi di Laurea in Ingegneria Biomedica (2009-2010) 186 pages.

Do et al., "Graphene and its one-dimensional patterns: from basic properties towards applications," Advances in Natural Sciences: Nanoscience and Nanotechnology, 1 (2010) 14 pages.

Fowler et al., "Practical Chemical Sensors from Chemically Derived Graphene," ACS Nano vol. 3, No. 2 (2009) pp. 301-306.

Geim et al., "The Rise of Graphene," Nature Materials, 6, (2007) pp. 183-191.

Longinotti, "Integrazione di biosensori microstrutturati in piattaforme microfluidiche per analisi in linea di metabolici," Tesi di Laurea in Ingegneria Chimica (2010-2011) 65 pages.

Massera et al., "Gas sensors based on graphene; Comparison of two different fabrication approaches," Chemistry Today, vol. 29, No. 1, Jan./Feb. 2011.

Menin et al., "Sintesi di film sol-gel nanostrutturati per sensori electrochimici ed ottici per gas inquinanti," Tesi Di Laurea, Universita degli Studi di Padova, Facolta di Ingegneria, (2010/2011) 151 pages.

Robinson et al., "Reduced Graphene Oxide Molecular Sensors," Nanoletters 2008, vol. 8, No. 10, pp. 3137-3140.

Schedin et al., "Detection of Individual Gas Molecules Adsorbed on Graphene," Nature Materials, 6 (2007) pp. 652-655.

Shao et al., "Graphene Based Electrochemical Sensors and Biosensors: A Review," Electroanalysis 2010, vol. 22, No. 10, pp. 1027-1036.

Stetter et al., "Artificial Chemical Sensing: Olfaction and the Electronic Nose," Proceedings of the Eighth International Symposium, The Electrochemical Society, Inc., Pennington, NJ (2001).

Yoon et al., "Carbon dioxide gas sensor using a graphene sheet," Elsevier Sensors and Actuators B 157 (2011) pp. 310-313.

\* cited by examiner

MANUFACTURING METHOD OF A GRAPHENE-BASED ELECTROCHEMICAL SENSOR, AND ELECTROCHEMICAL SENSOR

BACKGROUND

1. Technical Field

The present disclosure relates to a manufacturing method of a graphene-based electrochemical sensor and to an electrochemical sensor. In particular, the electrochemical sensor is integrated in a microfluidic system, and is obtained simultaneously with the steps of production of the microfluidic system itself.

2. Description of the Related Art

Molecule detectors have in the last few years witnessed a considerable development, finding widespread use in a vast range of fields, such as environmental monitoring, food analysis, diagnostics and, more recently, detection of toxic gases and explosive materials.

Notwithstanding the extraordinary potential of use, a considerable limitation of the sensors most commonly used regards the fact that they do not guarantee a sensitivity such as to enable measurement or detection of the presence of single atoms and/or single molecules. One of the main causes that renders problematical achievement of a high resolution is linked to the intrinsic thermal fluctuation in the materials and instruments used during the detection process, which generates an intrinsic noise higher than the useful signal that is to be detected.

In general, a sensor is a device that supplies to the user information on the surrounding environment in which the sensor itself is immersed. It is typically formed by a sensitive element, a transducer, and a data-acquisition system.

There may be distinguished, on the basis of the fields of application, physical sensors, chemical sensors, and biological sensors. A chemical sensor, in particular, is a device able to transform chemical information (such as the concentration of particular elements in the analytes) into a measurable quantity. Following upon the interaction between the analyte (which may be in the gaseous phase or in solution) and the active layer of the sensor, the sensor exerts a receptor and transducer function. The receptor function, which is a consequence of the interaction between the molecules to be detected and the active layer, causes a variation of the chemical and/or physical properties of the material that constitutes the active layer. The transducer function, which is a consequence of the aforementioned variation of the physical/chemical properties, transduces the chemical/physical modification of the active layer into a signal that can be processed, for example an electrical or optical signal.

Preferably, chemical sensors have a number of characteristics that can be summarized in: contained dimensions, presence of a layer able to react in contact with the analyte, sufficiently high speed of response, high capacity of selection of the species, high chemical stability over time and reversibility of the reactions, good mechanical properties of resistance to stresses, and capacity for generating signals of high intensity in the presence of gases or else detectable signals in the presence of small amounts of analytes.

Recently, the development of nanotechnologies applied to sensor systems has opened up new horizons, in particular via the introduction of organic materials deriving from graphite (such as, for example, fullerenes, carbon nanotubes, graphene). Sensor technologies that use thin films, for example made of graphene, have proven particularly effective for this purpose. See, for example, Deepak K. Pandey, Gyan Prakash, and Suprem R. Das, "Graphene Based Sensor Development"—Apr. 28, 2009, which is incorporated herein by reference in its entirety.

The electronic and mechanical properties of graphene are interesting for meeting the previous characteristics and implementing mechanisms of transduction that are particularly effective. The high chemical stability of the 2D lattice, the possibility of functionalizing the surface, the high mobility of the charge carriers (i.e., rapidity of response), the high surface-to-volume ratio, the high conductivity, a reduced defectiveness, and a considerable sensitivity to a wide range of analytes are some of the characteristics that render graphene a material of great interest for providing chemical and physical sensors.

Amongst the types of sensors based upon graphene, an interesting role is played by electrochemical sensors (in particular potentiometric, voltamperometric, conductometric sensors). For example, pH sensors exploit graphene as active channel of a FET, the gate terminal of which is controlled by an electrolytic solution, which plays the role of gate dielectric.

The ions present in the electrolyte cause a transfer of charge at the interface with the graphene that is reflected in a variation of the gate potential, thus modulating the passage of current in the transistor device.

Manufacture of a sensor in which the active layer is made of graphene presents considerably difficult aspects on account of the complexity of the process of synthesis and/or insulation of graphene, up to integration of the graphene layer in the architecture of the sensor.

Such a sensor can be used, for example, for the detection of molecules (analytes) in solution, and to determine the concentration of the molecules in a known volume of fluid. In this case, manufacture of the sensor integrated in a microfluidic system includes production of the sensing device, production of the microfluidic system, and bonding of the parts.

Typically, a microfluidic system is provided through the technique of soft lithography, which enables micro/nanostructured surfaces to be obtained with the use of elastomeric materials. This technique is very widespread and includes the production of a reference mold (master) structured in a way complementary to the fluidic structure that it is desired to obtain (replica) by transfer. The term "soft" regards the use of an elastomer that adapts to the mold replicating the structure thereof. Notwithstanding the great variety of materials available for said applications, the most widely used is PDMS (polydimethylsiloxane) thanks to its particular properties of transparency, biocompatibility, resistance to chemical attacks and to oxidation processes, high dielectric constant, good adhesion on smooth surfaces, high mechanical strength.

Even though it is the technique most widely used, production of the microfluidic system using PDMS typically employs a process flow that is rather long and articulated since it first creates the master (lithographically or electromechanically) and then creates the replica by laying the elastomeric pre-polymer on the master and induces crosslinking thereof by means of thermal treatment that activates the crosslinking agent mixed to the pre-polymer; and finally, separates the replica from the master, taking care not to deform or damage the microfluidic channels. The PDMS mold thus obtained is bonded to a glass made of boron silicate that functions as support and is set on top of the electronic device by means of a technique that includes activation of the surfaces to be bonded by means of an oxygen plasma to favor adhesion thereof, alignment of the two parts, and final pressing. Activation of the surfaces with the oxygen plasma generally renders bonding between the fluidic system and the electronic device irreversible.

BRIEF SUMMARY

According to one embodiment, a manufacturing method of a graphene-based electrochemical sensor and an electrochemical sensor are provided that are free from drawbacks of the known art.

One embodiment of the present disclosure is a manufacturing method of a graphene electrochemical sensor that includes providing a metal layer on a donor substrate; forming a graphene layer on the metal layer; forming a structural layer on the graphene layer; separating an intermediate structure that includes the structural layer and the graphene layer from the donor substrate by removing the metal layer; providing a final substrate including a first electrode and a second electrode extending on a first side of the final substrate; laminating the intermediate structure on the first side of the final substrate with the graphene layer in electrical contact with the first and second electrodes; and forming a fluidic path on the graphene layer by removing selective portions of the structural layer until the graphene layer is reached.

One embodiment of the present disclosure is an electrochemical sensor that includes a substrate having a first side; a first electrode and a second electrode extending over the first side of the substrate; a graphene layer extending over the first side of the substrate, in electrical contact with the first and second electrodes; a structural layer of dry resist, extending on the graphene layer; and a fluidic path extending through a thickness of the structural layer and on said graphene layer.

BRIEF DESCRIPTION OF THE SEVERAL VIEWS OF THE DRAWINGS

The disclosed embodiments are described, purely by way of non-limiting example, with reference to the attached drawings, wherein:

FIGS. 1a-1l show steps for manufacturing an electrochemical sensor according to an embodiment;

DETAILED DESCRIPTION

Figure 1A:
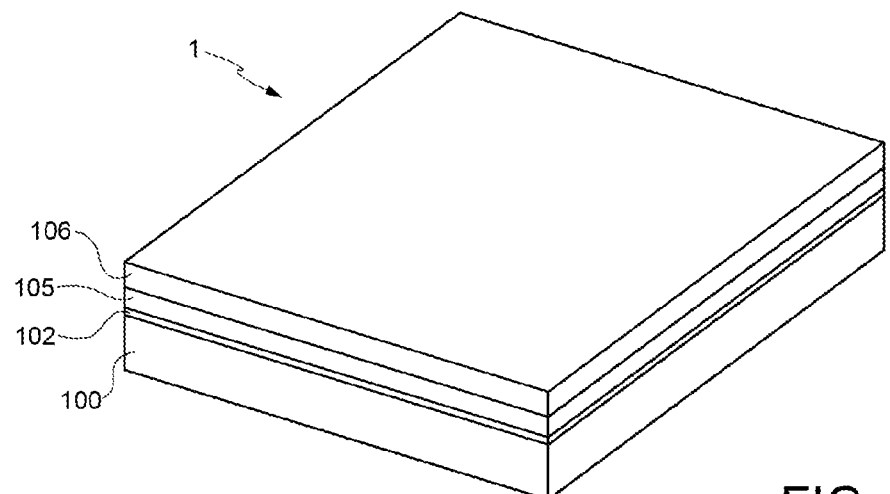

According to an embodiment, a manufacturing method of a graphene-based electrochemical sensor is provided, integrated in a microfluidic system provided with photosensitive resist in laminar form (dry resist), of a negative and permanent type.

According to an embodiment, a graphene layer, previously grown on a first substrate (in particular a metal substrate) with known techniques, is covered by a film or layer of dry resist. This layer of dry resist functions both as mechanical support for a subsequent step of transfer of the graphene onto a second substrate and as photosensitive layer used for the lithographic definition of micromachined fluidic channels.

Then, the first substrate is removed with wet chemical etching (in a way in itself known), and the layer of dry resist, together with the graphene layer, is transferred via a lamination process onto a second rigid or flexible substrate, of a generic size and shape.

Finally, in a subsequent process step, the dry resist is defined lithographically so as to form therein a microfluidic system (channels, chambers or trays for collection of fluids, in general the areas in which the solution to be analyzed is intended to flow and/or stay). The film of dry resist hence operates both as supporting layer for transfer of graphene, and as photosensitive layer, which can be defined lithographically, for the formation of the microfluidic structure.

According to one embodiment, graphene is grown on a metal layer with the CVD technique (or some other technique of growth or formation of a graphene layer).

According to an embodiment, the second substrate, onto which the graphene layer is transferred, is of a previously machined type. Said second substrate comprises metal contacts, and possibly dielectric contacts, which provide parts of one or more electronic devices (for example FETs—field-effect transistors) enabling creation of the electrochemical sensor and operation of said electrochemical sensor for the purpose of detecting a quantity that is to be measured (e.g., the pH of a solution). The electronic device formed on the second substrate is completed with the integration of graphene on the second substrate itself. In particular, the graphene layer forms the conduction channel of the FET and is the sensitive element (transducer) of the electrochemical sensor thus obtained.

The supporting layer for transfer of the graphene layer from the first substrate (substrate of growth or donor substrate) to the second substrate (final substrate, the latter being designed to carry both the microfluidic system and the detection electronics) is, as has been said, the dry resist. Following upon the step of transfer of graphene onto the final substrate, and upon lithographic definition of the microfluidic channels/chambers in the same dry resist as the one used for transfer of the graphene, lamination of a further layer of dry resist is carried out, which enables encapsulation, where appropriate, of the microfluidic structures defined previously. At the same time access to said channels/chambers is created by opening lithographically the dry resist on the inlet and outlet channels.

It is evident that on one and the same final substrate there may be formed a plurality of electronic devices (even different from one another), each of which is electrically insulated from the others. This is rendered possible by the fact that the graphene layer can be easily removed by means of chemical etching in oxygen plasma. It is thus possible, starting from a single graphene layer transferred onto the final substrate, to form for example a plurality of FETs, each of which having a graphene channel of its own electrically insulated from the other FETs.

The dry resist in which the microfluidic system is defined is rendered permanent and chemically stable by means of thermal treatment (typically at temperatures comprised between approximately 150° C. and approximately 200° C.).

With reference to FIGS. 1a-1l, an embodiment is now described in detail.

In particular, the steps of a method for transfer of the graphene from the substrate of growth onto the final substrate are shown, simultaneously with steps of formation of microfluidic channels/chambers integrated in the electrochemical sensor.

The disclosed embodiments can be implemented in practice with the techniques for manufacturing integrated circuits currently used in the sector. In describing various embodiments, for brevity, many process steps that are not necessary for an understanding of the embodiments are omitted from the description.

Moreover, the figures show schematic views of the integrated structure during the manufacturing steps, and not are represented in scale, but instead are represented so as to emphasize important characteristics of the process.

With reference to FIG. 1a, a support is provided of generic size, shape, and thickness, in particular a wafer 1, including a donor substrate 100, for example a semiconductor or insulating crystalline substrate, a semiconductor-device substrate, an epitaxial layer, a flexible substrate, a metal film, or an organic-device substrate, just to cite some examples.

The donor substrate 100 comprises a metal layer 102 such as a nickel layer or a copper layer, formed on the donor substrate 100 with known techniques (for example, techniques of evaporation or chemical vapor deposition).

On the metal layer 102 a graphene layer 105 is grown via a technique of chemical vapor deposition (CVD), according to the known art.

However, other techniques of formation of the graphene layer 105 on a donor substrate 100 are possible.

Next, laminated on the graphene layer 105 is a structural layer 106, in particular a film of dry resist. The structural layer 106 has a thickness comprised between some micrometers (for example, 10 μm) and hundreds of micrometers (for example, 200 μm).

The dry resist is a photosensitive, negative, and permanent, material, for example comprising 25-35% of acrylic ester, 65-75% of acrylic polymer, and 1-10% of cross-linking agents. It is evident that other types of photosensitive and permanent dry resist can be used.

Figure 1B:
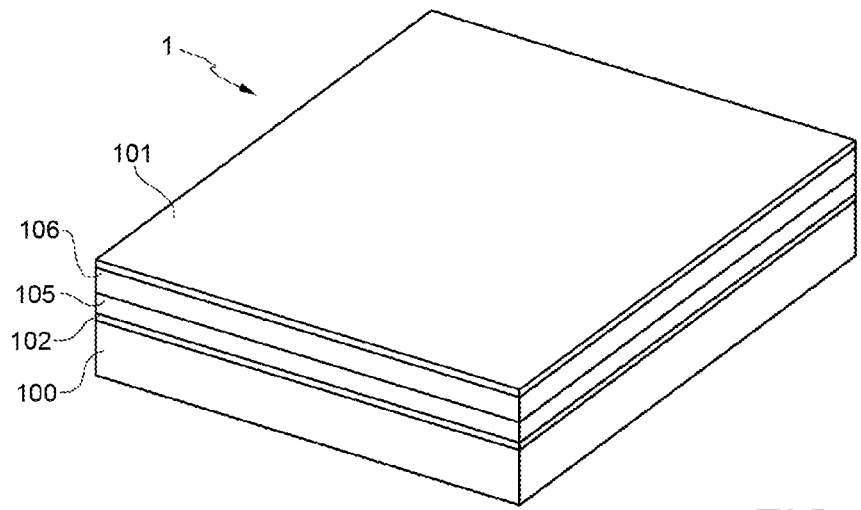
Figure 1C:
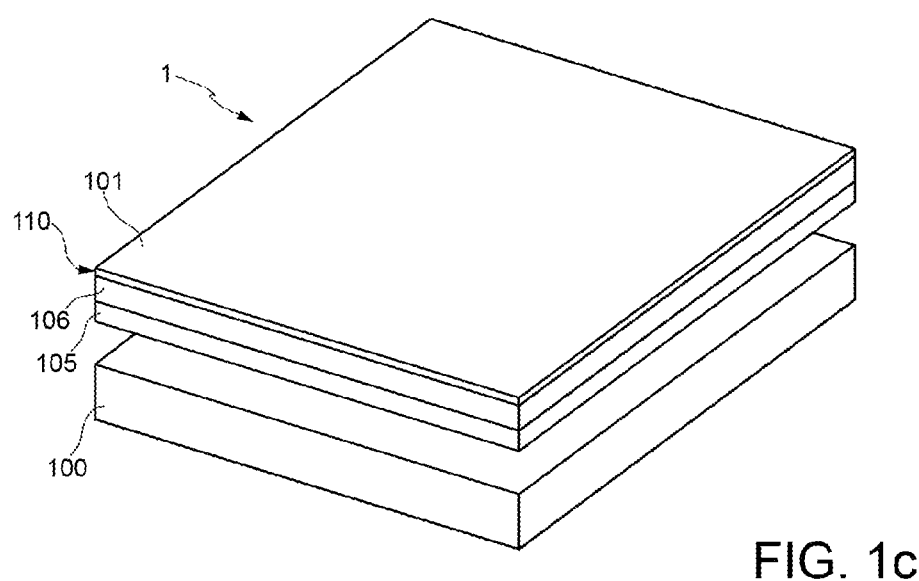

With reference to FIG. 1b, laminated on top of the film of dry resist 106 is a thermal-release adhesive tape 101. In particular, this step of lamination of the adhesive tape is carried out at room temperature.

Then (FIG. 1c), the metal layer 102 is chemically etched in liquid solution (wet etching), for example by setting the wafer 1 in a 1-M bath of iron (III) chloride ($FeCl_3$) in water, according to known techniques. This step enables uncoupling of the donor substrate 100 from an intermediate structure 110 comprising the adhesive tape 101, the film of dry resist 106, and the graphene layer 105.

Then (FIG. 1d), a final substrate 104 is provided having a top surface 104a and a bottom surface 104b, opposite to one another. The final substrate 104 is a semiconductor or insulating crystalline substrate, a flexible substrate, for example made of plastic, or some other substrate still.

According to one embodiment, the final substrate 104 is of a previously machined type, and in particular comprises a plurality of electrodes 130, 131, for example in the form of pads of conductive material (for example metal such as gold), extending over the top surface 104a of the final substrate 104. The electrodes 130, 131 are formed in pairs, where each pair of electrodes 130 131, provides, according to one embodiment, source and drain terminals of a respective field-effect transistor.

In order to connect together the two electrodes 130, 131, the graphene layer 105 is laminated on the top surface 104a of the final substrate 104, in direct electrical contact with the electrodes 130, 131.

In particular, laminated on the top surface 104a of the final substrate 104 is the intermediate structure 110 including the tape 101, the film of dry resist 106, and the graphene layer 105.

Then (FIG. 1e), the final substrate 104, carrying the intermediate structure 110, is subject to thermal treatment on hot plate or in oven at a temperature comprised between 80° C. and 120° C. (preferably 100° C.) so as to promote spontaneous release of the adhesive tape 101.

A structure 107 comprising the film of dry resist 106, the graphene layer 105, and the final substrate 104 is thus obtained.

According to one embodiment, the graphene layer transferred is a graphene monolayer. Moreover, the graphene layer 105 transferred has a maximum dimension that depends only upon the size of the original graphene sheet.

According to a further embodiment, the graphene layer 105 transferred is compact and free from polymeric contaminants.

Then (FIG. 1f), steps of lithographic definition and selective removal of the film of dry resist 106 are carried out to obtain the channels, the chambers for containment of liquids, and the inlet and outlet regions of the microfluidic system.

The shape and extension of the microfluidic channels/chambers can vary according to the desired application and does not form the subject, in itself, of the disclosed embodiments. By way of example, FIG. 1f shows a lithographic mask 109 for a negative dry resist, where the shape of the channels and of the chamber is defined, on the mask 109, by means of an opaque area.

Following upon exposure of the film of dry resist 106 to UV light (source 111), a step of wet chemical etching is carried out to remove selective portions of the film of dry resist 106 so as to form (FIG. 1g), a containment chamber 120, channels 121, 122, an inlet region 126, and an outlet region 128 extending in depth in the film of dry resist 106, throughout the thickness of the latter.

The containment chamber 120 is connected, by means of the channels 121, 122, to the inlet region 126 and to the outlet region 128, respectively.

Figure 1D:
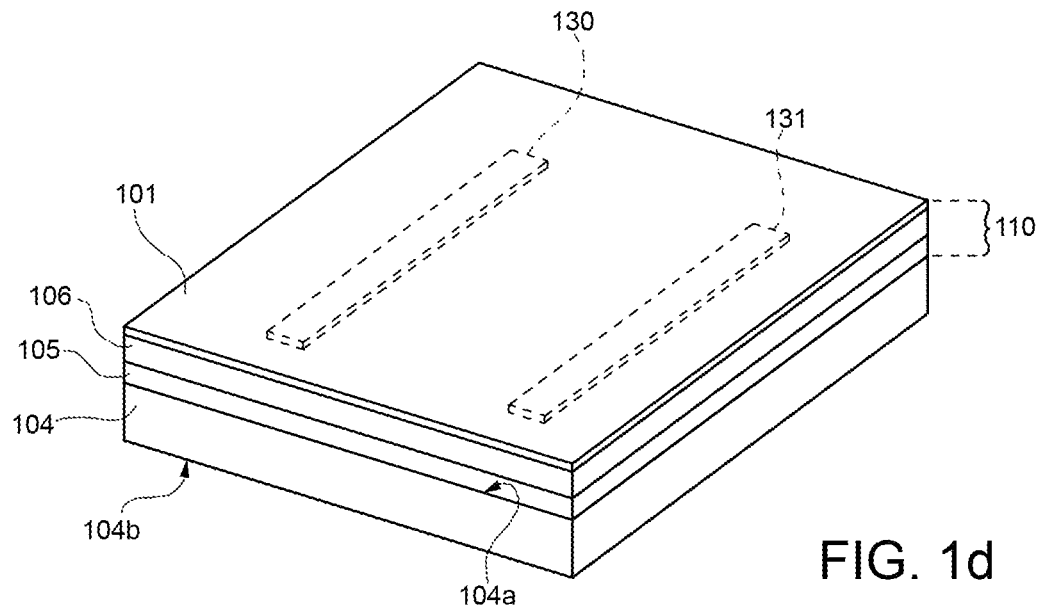
Figure 1E:
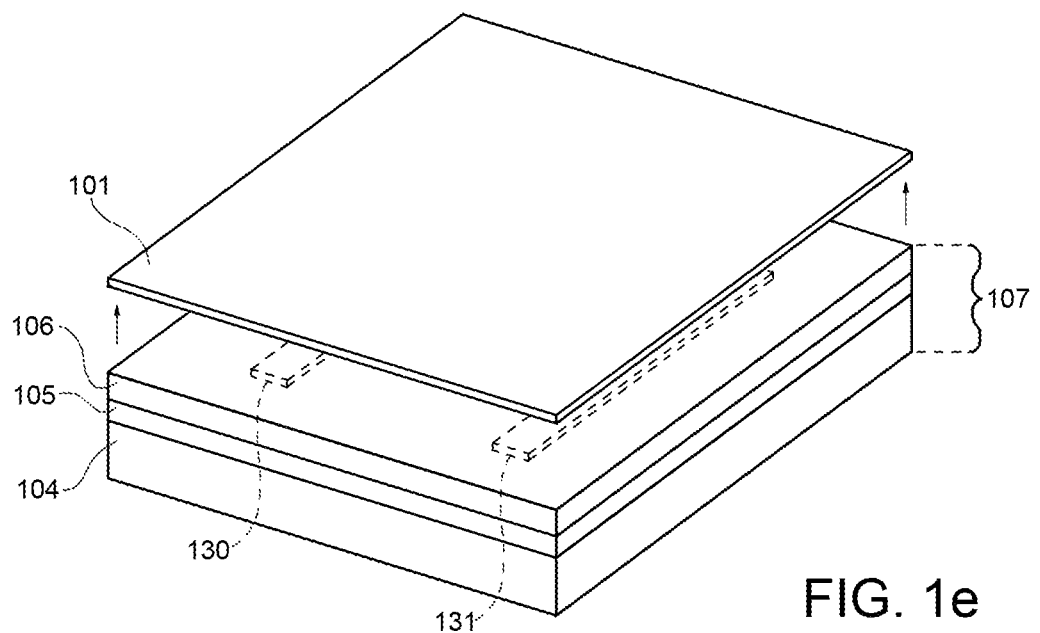
Figure 1F:
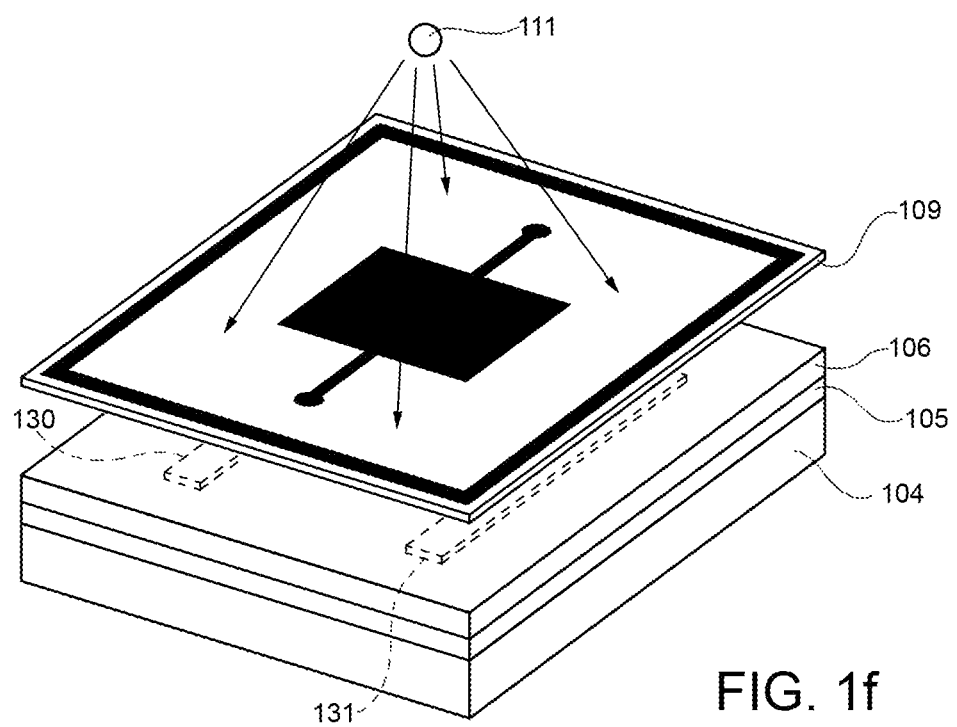
Figure 1G:
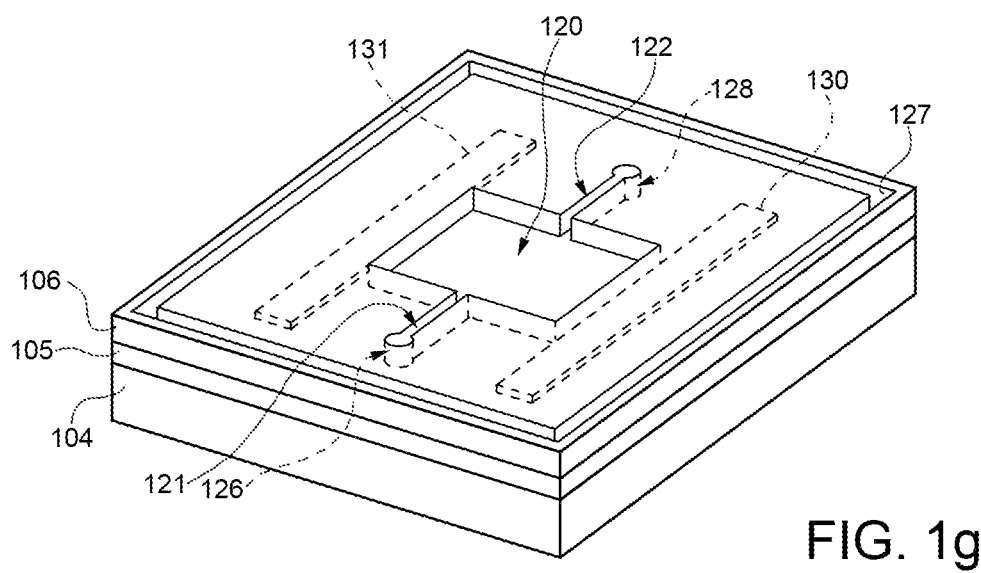

During the steps represented in FIGS. 1f and 1g, it is moreover possible to define lithographically a frame 127 that completely surrounds the channels 121, 122, the containment chamber 120, the inlet region 126 and outlet region 128, and the first and second electrodes 130, 131. The etching step of FIG. 1g comprises selective removal of portions of the film of dry resist 106 to form a trench that provides the frame 127, and expose the underlying graphene portion.

Since the step of FIG. 1g comprises selective removal of portions of the film of dry photoresist 106 throughout the thickness of the film of dry photoresist 106 itself, surface portions of the graphene layer 105 extending underneath the containment chamber 120, the channels 121, 122, and the inlet region 126 and outlet region 128 are exposed.

It is evident that it is possible to form (in a way not shown) a plurality of containment chambers 120 fluidically coupled together by means of respective channels. According to a different embodiment, the containment chambers 120 can be fluidically isolated from one another, according to the need. It is likewise possible for some containment chambers 120 to be fluidically connected together and other containment chambers 120 to be fluidically isolated from one another.

It is moreover evident that it is possible to omit the outlet region 128 in the case where the electrochemical sensor is of a disposable type.

According to an embodiment, in which the final substrate 104 has the first and second electrodes 130, 131 formed prior to the step of FIG. 1d, the containment chamber 120 is formed, when considered in top plan view, in a region comprised between the first and second electrodes 130, 131.

Figure 1H:
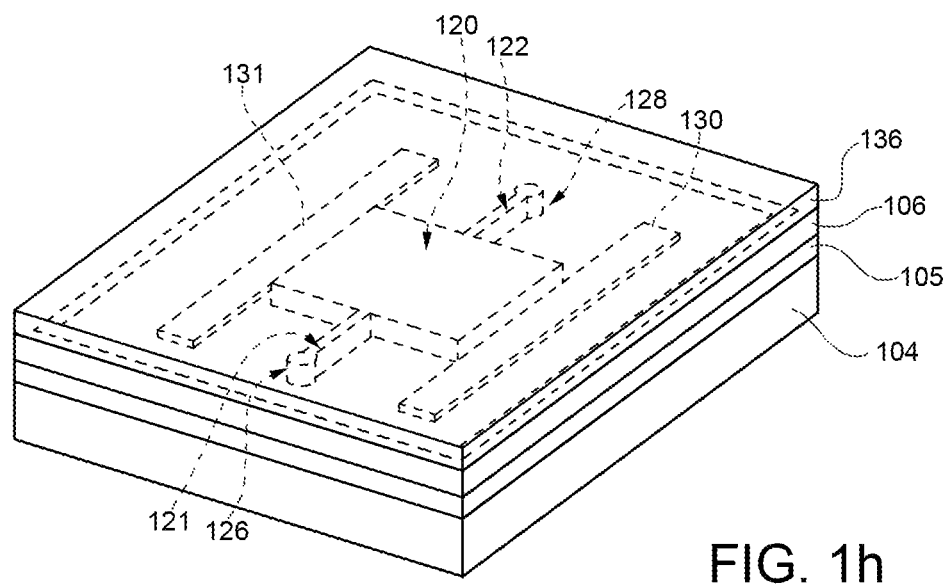

With reference to FIG. 1h, a cover layer (or cover sheet) 136 is formed on top of the film of dry resist 106. According to one embodiment, the cover layer 136 is a layer of dry resist similar to the film of dry resist 106 and is made, in particular, of the same material. In this case, the cover layer 136 is formed by lamination. The thickness of the cover layer 136 is, for example, comprised between some micrometers (for example, 10 μm) and hundreds of micrometers (for example, 200 μm).

Next (FIGS. 1*i* and 1*j*), a step of lithographic definition and wet chemical etching of the cover layer 136 is carried out to form, through the cover layer 136, the access channels 133, 134 for fluidic access to the inlet region 126 and outlet region 128. In this way, the inlet region 126 and outlet region 128 are fluidically accessible from outside the electrochemical sensor, for supply of an analyte in liquid solution to the chamber 120, through the channel 121.

Figure 1I:
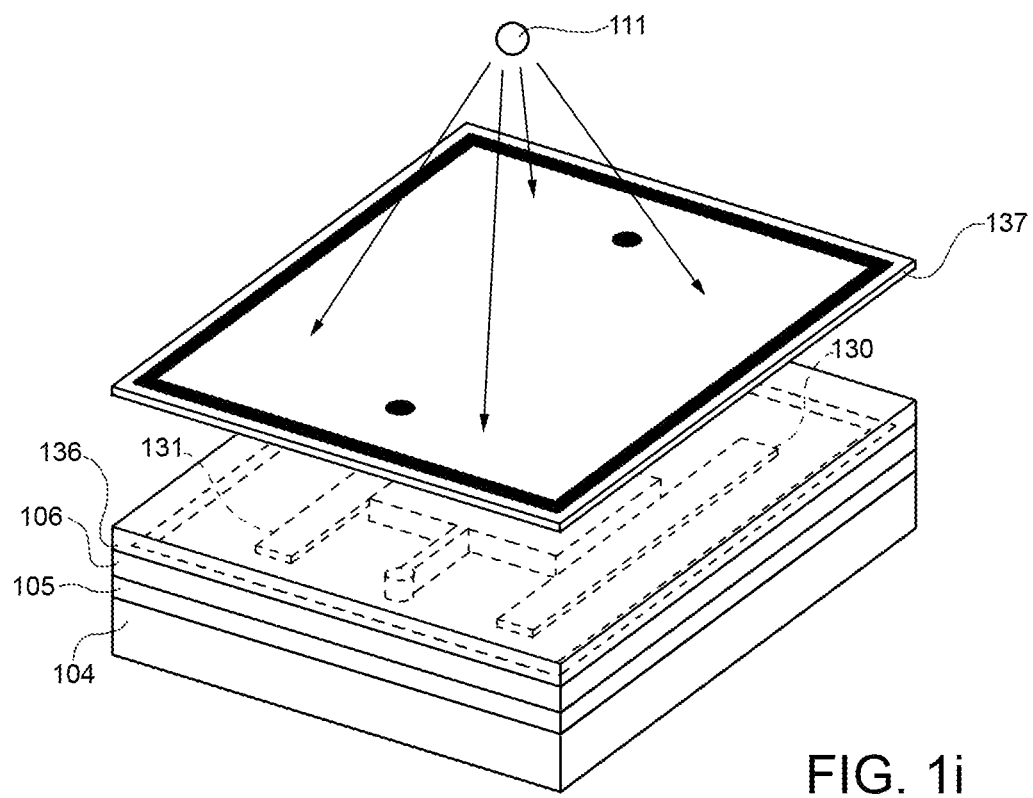

During the step of FIG. 1*i* it is moreover possible to define (e.g., lithographically) a frame 138 aligned, along the axis Z, to the frame 127, and completely surrounding the channels 121, 122, the containment chamber 120, the inlet region 126 and outlet region 128, and the first and second electrodes 130, 131.

Figure 1J:
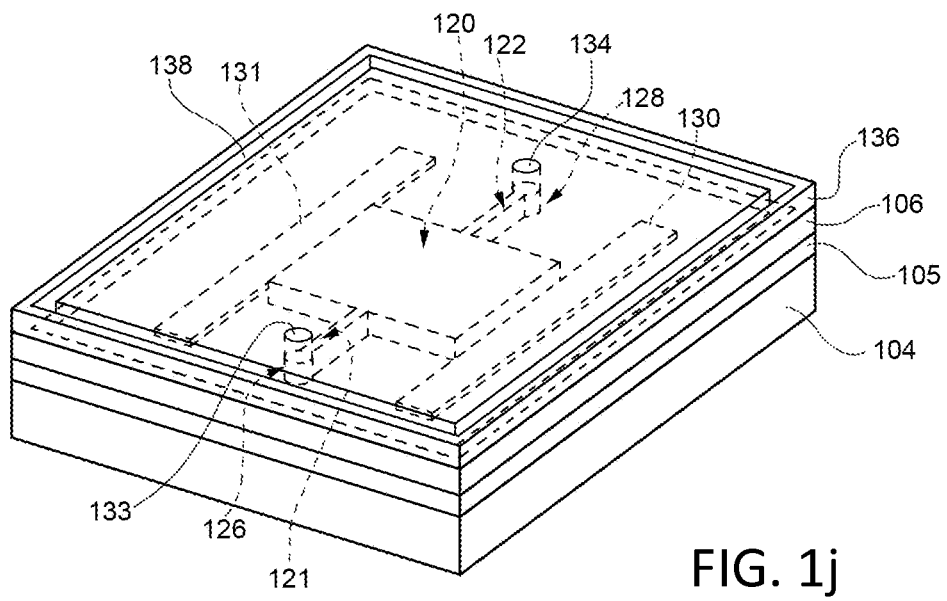

The etching step of FIG. 1*j* further comprises removal of the frame portion of dry resist 138 to expose the underlying graphene portion.

Then (FIG. 1*k*), a step of oxygen-plasma chemical etching is carried out to remove the graphene exposed in the step of FIG. 1*j*. In particular, the graphene is removed in an area corresponding to the frame formed previously, thus electrically insulating the sensor. During the same step, the exposed graphene is removed via the access channels 133, 134 from the inlet region 126 and outlet region 128.

Figure 1K:
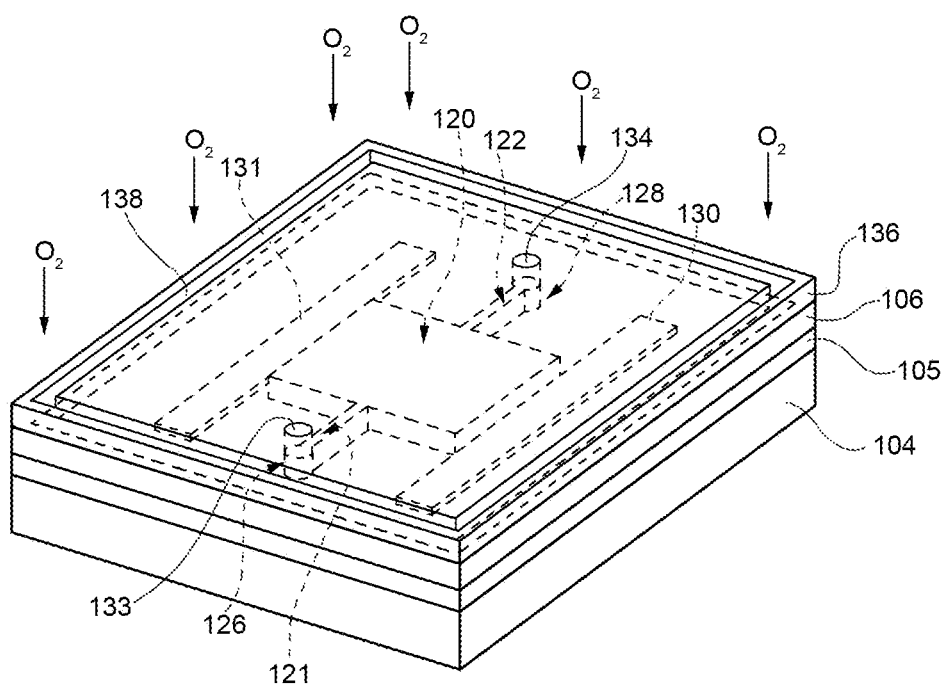
Figure 1I:
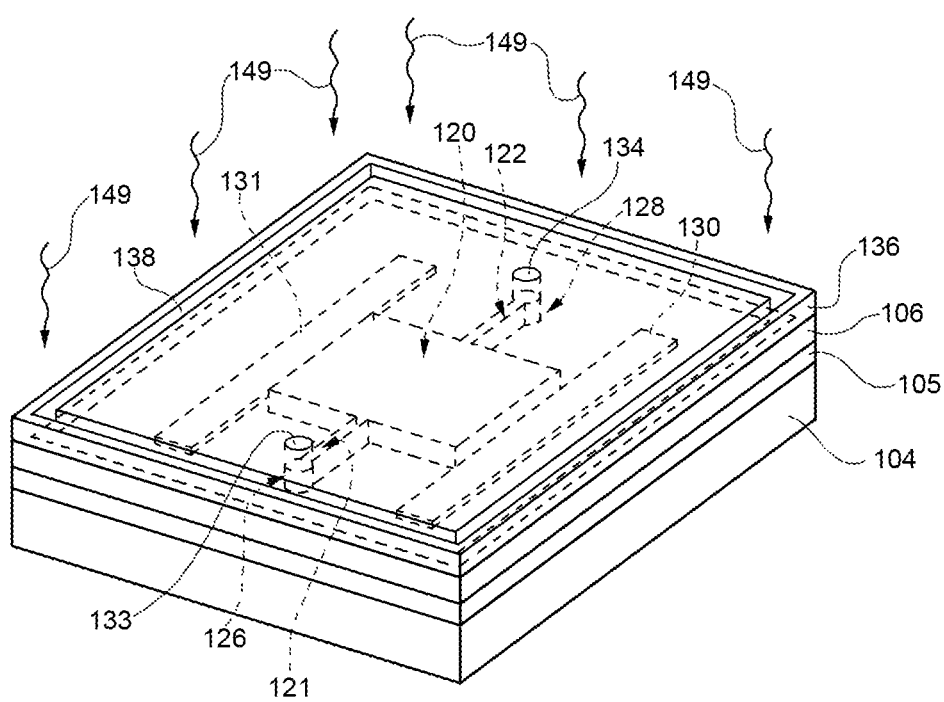

There is thus formed, during the step of FIG. 1*k*, an insulation frame 140, formed by the frames 127 and 138. In the case where the wafer comprises a plurality of electrochemical sensors, the step of FIG. 1*k* enables electrical insulation of said electrochemical sensors with respect to one another.

The first and second electrodes 130, 131 are electrically coupled together by means of the portion of graphene layer extending inside the insulation frame 140, which forms, in use and according to an embodiment, a conductive channel of a FET.

With reference to FIG. 1*l*, a step of curing (typically at temperatures ranging from approximately 150° C. to approximately 200° C.) is carried out as schematically represented by arrows 149, to render the film of dry resist 106, permanent and structurally/chemically stable. During this curing step, also the cover layer 136 is rendered permanent and structurally/chemically stable.

Figure 2:
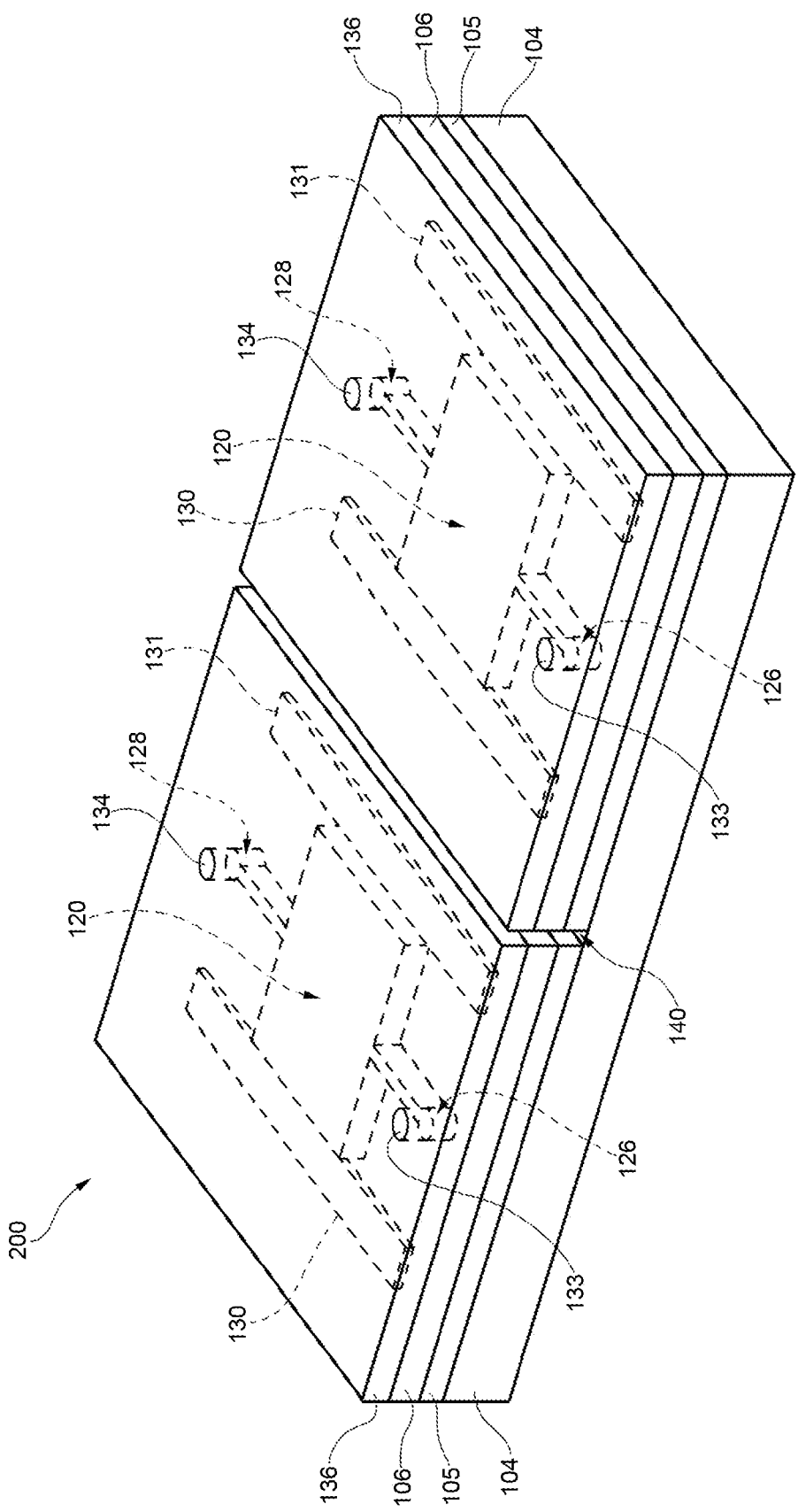
FIG. 2 shows, in perspective view, an electrochemical sensor at the end of the manufacturing steps of FIGS. 1a-1l.

FIG. 2 shows, in perspective view, a schematic representation of an electrochemical sensor 200, in particular integrated in a microfluidic system, at the end of the machining steps according to FIGS. 1*a*-1*l*.

Figure 4A:
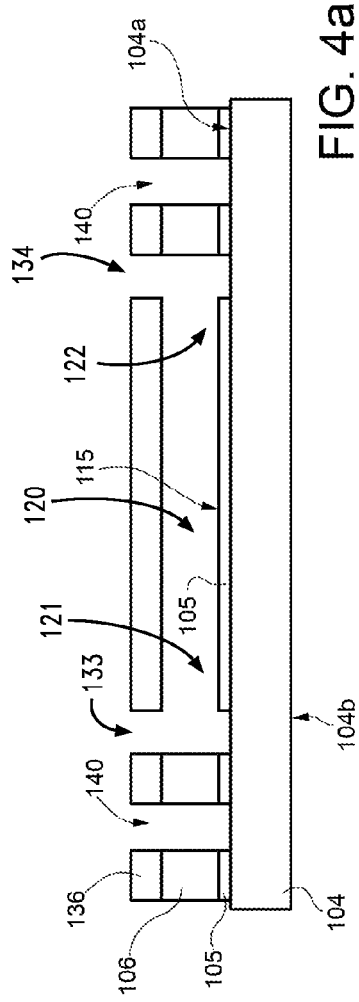
FIG. 4a shows the electrochemical sensor of FIG. 2 in lateral cross section along the line of section A-A of FIG. 3.
Figure 4B:
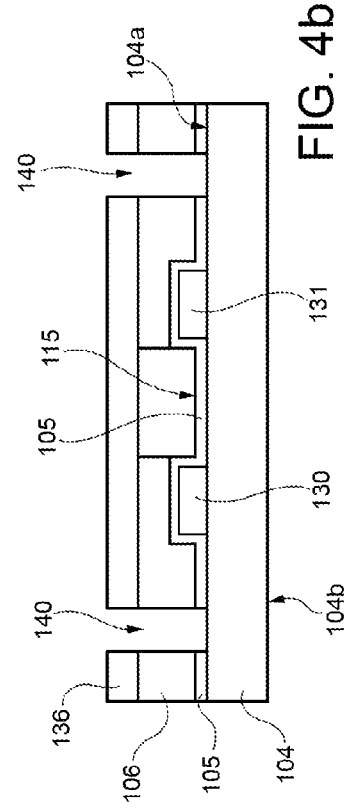
FIG. 4b shows the electrochemical sensor of FIG. 2 in lateral cross section along the line of section B-B of FIG. 3.
Figure 3:
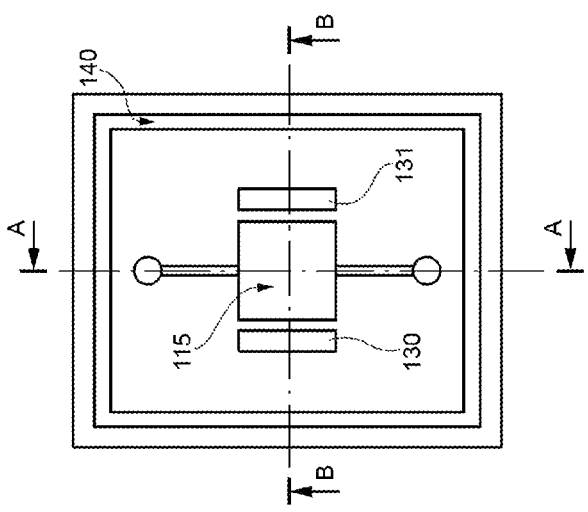
FIG. 3 shows, in a top plan view, the electrochemical sensor of FIG. 2.

FIG. 3 shows a top plan view of the electrochemical sensor 200 at the end of the steps of machining according to FIGS. 1*a*-1*l*. FIG. 4*a* shows a cross-sectional view of the sensor of FIG. 3, taken along the line of section A-A of FIG. 3. FIG. 4*b* shows a further cross-sectional view of the sensor of FIG. 3, taken along the line of cross section B-B of FIG. 3.

With joined reference to FIGS. 2, 3, 4*a* and 4*b*, the electrochemical sensor 200 comprises, in particular, the substrate 104 carrying the first and second electrodes 130, 131, and a channel region 115, made of graphene (obtained following upon the steps of machining of the graphene layer 105 described previously), which extends over the top surface 104*a* of the substrate 104 and over the first and second electrodes 130, 131.

The channel region 115 extends, in particular, on the top surface 104*a* of the substrate 104 in the region of the latter comprised between the electrodes 130, 131. As a consequence of the manufacturing steps previously described, the graphene layer that forms the channel region 115 extends also outside the region comprised between the electrodes 130, 131, in particular over the entire top surface 104*a* of the substrate 104, except for the areas corresponding to the inlet region 126 and outlet region 128 and the frame-insulation region 140 that surrounds the electrochemical sensor 200.

Extending above the substrate 104 and the channel region 115 is the film of dry resist 106, in which the containment chamber 120 is formed, which, in turn, extends above the channel region 115. In particular the containment chamber 120 is aligned, along the axis Z, to the channel region 115. Moreover formed in the film of dry resist 106 are the channels 121, 122, which connect, respectively, the inlet region 126 and the outlet region 128 to the containment chamber 120.

Extending over the film of dry resist 106 is the cover layer 136, designed to seal the containment chamber 120 and the channels 121 and 122 at the top. The inlet region 126 and outlet region 128 are rendered fluidically accessible from outside the electrochemical sensor 200 by means of the access channels 133, 134, which extend right through the cover layer 136 until the inlet region 126 and outlet region 128 are, respectively, reached.

Figure 5:
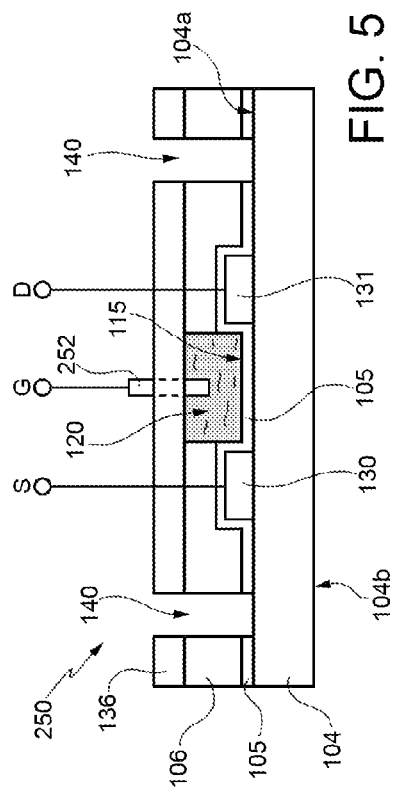
FIG. 5 shows the electrochemical sensor of FIG. 4b having a FET, according to one embodiment.

FIG. 5 shows a measurement system 250 including the electrochemical sensor 200 of FIGS. 2, 3, 4*a*, 4*b*.

In use, an electrolytic solution is introduced, for example by means of a micropipette, into the inlet region 126 via the access channel 133. The electrolytic solution then flows towards the containment chamber 120. As a result of the electrical interaction of the electrolytic solution with the graphene channel region 115, information is obtained on the analyte present in the containment chamber 120.

For example, using the electrochemical sensor 200 as pH sensor, the channel region 115 is used as active channel of a FET, where the source terminal S is, for example, the electrode 130, the drain terminal D is the electrode 131, and the gate terminal G is controlled through the electrolytic solution itself. For this purpose, a gate electrode 252 is provided set in contact with the electrolytic solution.

The gate electrode 252 is introduced into the containment tray 120 for example through an opening formed through the cover layer 136. Alternatively, the cover layer 136 can be omitted so that the containment chamber 120 is easily accessible from outside.

The gate potential is affected by the transfer of charge at the graphene/electrolytic solution interface on account of the ions present in the electrolytic solution, thus modulating the passage of current between the two source S and drain D electrodes of the transistor. The analytical information is consequently obtained from the electrical signal resulting from the interaction of the analyte with the graphene layer 105.

From an examination of the characteristics of the disclosed embodiments, the advantages that they afford are evident.

The use of a resist in laminar form simultaneously enables transfer of the graphene and lithographic definition of the microfluidic system. The process flow does not require application of any bonding technique, which might prove harmful for the integrity of the graphene. The procedure can be scaled over an extensive area or roll-to-roll. The method and instrumentation used enable transfer onto substrates of any type, size and shape. The absence of a strong mechanical action enables extension of the method to substrates that are brittle, thin, or flexible. The process can be industrialized, since it presupposes the use of equipment commonly used in the semiconductor industry. The use of a single material (dry resist) as transfer layer and as layer that can be defined lithographically preserves the graphene from mechanical stresses. The flexibility of the dry resist and its capacity for adhering to substrates of various types enables application of the method, according to various embodiments, to plastic substrates for providing flexible devices.

Finally, the use of dry bio-compatible resists enables application of the disclosed methods to the production of devices that can be used in the bio-medical field, for biological analyses.

Finally, it is clear that modifications and variations may be made to what has been described and illustrated herein, without thereby departing from the sphere of protection of the present disclosure.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An electrochemical sensor, comprising:
   a substrate having a first side;
   a first electrode and a second electrode extending over the first side of the substrate;
   a graphene layer extending over the first side of the substrate, in electrical contact with the first and second electrodes;
   a structural layer of dry resist, extending on the graphene layer; and
   a fluidic path extending through a thickness of the structural layer and on said graphene layer, wherein the fluidic path is disposed entirely between the first and second electrodes.

2. The sensor according to claim 1, wherein the structural layer extends in direct contact with the graphene layer and has a thickness from 10 μm to 200 μm.

3. The sensor according to claim 1, wherein the fluidic path comprises:
   a well positioned on top of, and aligned with, said graphene layer, the graphene layer forming a bottom wall of said well;
   an inlet region that provides an inlet point for a fluid to be supplied to the well; and
   a supply channel fluidically coupled to the inlet region and to the well.

4. The sensor according to claim 1, further comprising a cover layer extending over and sealing a top of said fluidic path.

5. The sensor according to claim 4, wherein the cover layer is made of dry resist.

6. The sensor according to claim 1, further comprising an insulating frame defined in the graphene layer and completely surrounding the first and second electrodes and the fluidic path.

7. The sensor according to claim 1, wherein the first and second electrodes form, respectively, a first conduction terminal and a second conduction terminal of a field-effect transistor, said graphene layer extending between the first and second electrodes and forming a channel of said field-effect transistor.

8. The sensor according to claim 1, wherein the graphene layer forms, together with the first and second electrodes, a field-effect transistor, said sensor being a pH sensor.

9. A measurement system, comprising:
   an electrochemical sensor that includes:
      a substrate having a first side;
      a first electrode and a second electrode extending over the first side of the substrate;
      a graphene layer extending over the first side of the substrate, in electrical contact with the first and second electrodes;
      a structural layer of dry resist, extending on the graphene layer; and
      a fluidic path extending through a thickness of the structural layer and on said graphene layer, wherein the fluidic path is disposed entirely between the first and second electrodes;
   a gate terminal in contact with the fluidic path, the gate terminal being part of a field effect transistor that includes a channel region of the graphene layer, and the first and second electrodes as source and drain regions, respectively.

10. The measurement system according to claim 9, wherein the structural layer extends in direct contact with the graphene layer and has a thickness from 10 μm to 200 μm.

11. The measurement system according to claim 9, wherein the fluidic path comprises:
   a well positioned on top of, and aligned with, said graphene layer, the graphene layer forming a bottom wall of said well;
   an inlet region that provides an inlet point for a fluid to be supplied to the well; and
   a supply channel fluidically coupled to the inlet region and to the well.

12. The measurement system according to claim 9, further comprising a cover layer extending over and sealing a top of said fluidic path, wherein the gate electrode extends through the cover layer.

13. The measurement system according to claim 12, wherein the cover layer is made of dry resist.

14. The measurement system according to claim 9, further comprising an insulating frame defined in the graphene layer and completely surrounding the first and second electrodes and the fluidic path.

15. A method of forming electrochemical sensor, the method comprising:
   forming a first electrode and a second electrode extending over a first side of a substrate;
   forming a graphene layer extending over the first side of the substrate, in electrical contact with the first and second electrodes;
   forming a structural layer of dry resist, extending on the graphene layer; and
   forming a fluidic path entirely between the first and second electrodes and extending through a thickness of the structural layer and on said graphene layer.

16. The method according to claim 15, wherein forming the structural layer includes forming the structural layer with a thickness from 10 μm to 200 μm in direct contact with the graphene layer.

17. The method according to claim 15, wherein forming the fluidic path comprises:
   forming a well positioned on top of, and aligned with, said graphene layer, the graphene layer forming a bottom wall of said well;
   forming an inlet region that provides an inlet point for a fluid to be supplied to the well; and
   forming a supply channel fluidically coupled to the inlet region and to the well.

18. The method according to claim 15, further comprising forming a cover layer extending over and sealing a top of said fluidic path.

19. The method according to claim 18, wherein the cover layer is made of dry resist.

20. The method according to claim 15, further comprising forming an insulating frame defined in the graphene layer and completely surrounding the first and second electrodes and the fluidic path.

21. The method according to claim 15, wherein the first and second electrodes form, respectively, a first conduction terminal and a second conduction terminal of a field-effect transistor, said graphene layer extending between the first and second electrodes and forming a channel of said field-effect transistor.

22. The method according to claim 15, wherein the graphene layer forms, together with the first and second electrodes, a field-effect transistor, said sensor being a pH sensor.

23. An electrochemical sensor, comprising:
- a substrate having a first side;
- a first electrode and a second electrode extending over the first side of the substrate;
- a graphene layer extending over the first side of the substrate, in electrical contact with the first and second electrodes;
- a structural layer of dry resist, extending on the graphene layer, wherein the structural layer extends in direct contact with the graphene layer and has a thickness from 10 μm to 200 μm; and
- a fluidic path extending through a thickness of the structural layer and on said graphene layer.

24. The sensor according to claim 23, wherein the fluidic path comprises:
- a well positioned on top of, and aligned with, said graphene layer, the graphene layer forming a bottom wall of said well;
- an inlet region that provides an inlet point for a fluid to be supplied to the well; and
- a supply channel fluidically coupled to the inlet region and to the well.

25. The sensor according to claim 23, further comprising a cover layer extending over and sealing a top of said fluidic path.

26. A measurement system, comprising:
an electrochemical sensor that includes:
- a substrate having a first side;
- a first electrode and a second electrode extending over the first side of the substrate;
- a graphene layer extending over the first side of the substrate, in electrical contact with the first and second electrodes;
- a structural layer of dry resist, extending on the graphene layer wherein the structural layer extends in direct contact with the graphene layer and has a thickness from 10 μm to 200 μm; and
- a fluidic path extending through a thickness of the structural layer and on said graphene layer; and
- a gate terminal in contact with the fluidic path, the gate terminal being part of a field effect transistor that includes a channel region of the graphene layer, and the first and second electrodes as source and drain regions, respectively.

27. The measurement system to claim 26, wherein the fluidic path comprises:
- a well positioned on top of, and aligned with, said graphene layer, the graphene layer forming a bottom wall of said well;
- an inlet region that provides an inlet point for a fluid to be supplied to the well; and
- a supply channel fluidically coupled to the inlet region and to the well.

28. The measurement system to claim 26, further comprising a cover layer extending over and sealing a top of said fluidic path.

29. A method of forming electrochemical sensor, the method comprising:
- forming a first electrode and a second electrode extending over a first side of a substrate;
- forming a graphene layer extending over the first side of the substrate, in electrical contact with the first and second electrodes;
- forming a structural layer of dry resist, extending on the graphene layer, wherein forming the structural layer includes forming the structural layer with a thickness from 10 μm to 200 μm in direct contact with the graphene layer; and
- forming a fluidic path extending through a thickness of the structural layer and on said graphene layer.

30. The method according to claim 29, wherein forming the fluidic path comprises:
- forming a well positioned on top of, and aligned with, said graphene layer, the graphene layer forming a bottom wall of said well;
- forming an inlet region that provides an inlet point for a fluid to be supplied to the well; and
- forming a supply channel fluidically coupled to the inlet region and to the well.

31. The method according to claim 29, further comprising forming a cover layer extending over and sealing a top of said fluidic path.

* * * * *